(12) United States Patent
Schumann

(10) Patent No.: US 6,737,080 B1
(45) Date of Patent: May 18, 2004

(54) COMPOSITE LAMINATE AND METHOD FOR ITS PRODUCTION

(75) Inventor: Klaus Schumann, Neuwied (DE)

(73) Assignee: LTS Lohmann Therapie-Systeme AG, Andernach (DE)

(*) Notice: Subject to any disclaimer, the term of this patent is extended or adjusted under 35 U.S.C. 154(b) by 0 days.

(21) Appl. No.: 09/979,704

(22) PCT Filed: May 17, 2000

(86) PCT No.: PCT/EP00/04459
§ 371 (c)(1), (2), (4) Date: Feb. 13, 2002

(87) PCT Pub. No.: WO00/74933
PCT Pub. Date: Dec. 14, 2000

(30) Foreign Application Priority Data

Jun. 4, 1999 (DE) .......................... 199 25 613

(51) Int. Cl.⁷ .................. A61F 13/00; A61F 13/02; A61L 15/16
(52) U.S. Cl. .................. 424/449; 424/443; 424/448
(58) Field of Search .................. 424/449, 443, 424/448

(56) References Cited

U.S. PATENT DOCUMENTS 4,781,924 A * 11/1988 Lee et al. .................... 424/449
5,225,199 A * 7/1993 Hidaka et al. ............... 424/443
5,230,896 A * 7/1993 Yeh et al. .................... 424/443

FOREIGN PATENT DOCUMENTS

| DE | 42 37 453 C1 | 8/1993 |
| DE | 19 64 6048 | 5/1998 |
| EP | 0 307 187 A2 | 3/1989 |
| WO | WO 96/19976 A1 | 7/1996 |

OTHER PUBLICATIONS

Y. W. Chien, "Developmental Concepts and Practice in Transdermal Therapeutic Systems" in Y. W. Chien, *Transdermal Controlled Systemic Medications*, Marcel Dekker Inc., New York (1982), Chapter 2, p. 25–81.

* cited by examiner

Primary Examiner—Thurman K. Page
Assistant Examiner—Isis Ghali
(74) Attorney, Agent, or Firm—ProPat, L.L.C.

(57) ABSTRACT

The invention relates to a composite laminate, especially a transdermal therapeutic system (TTS) that contains in at least one layer a component that is sensitive to moisture. Said system further comprises one layer that is spatially separate from said at least one moisture-sensitive layer and that is capable of absorbing moisture. The spatial separation can be achieved by means of a horizontal or vertical separation layer.

15 Claims, 4 Drawing Sheets

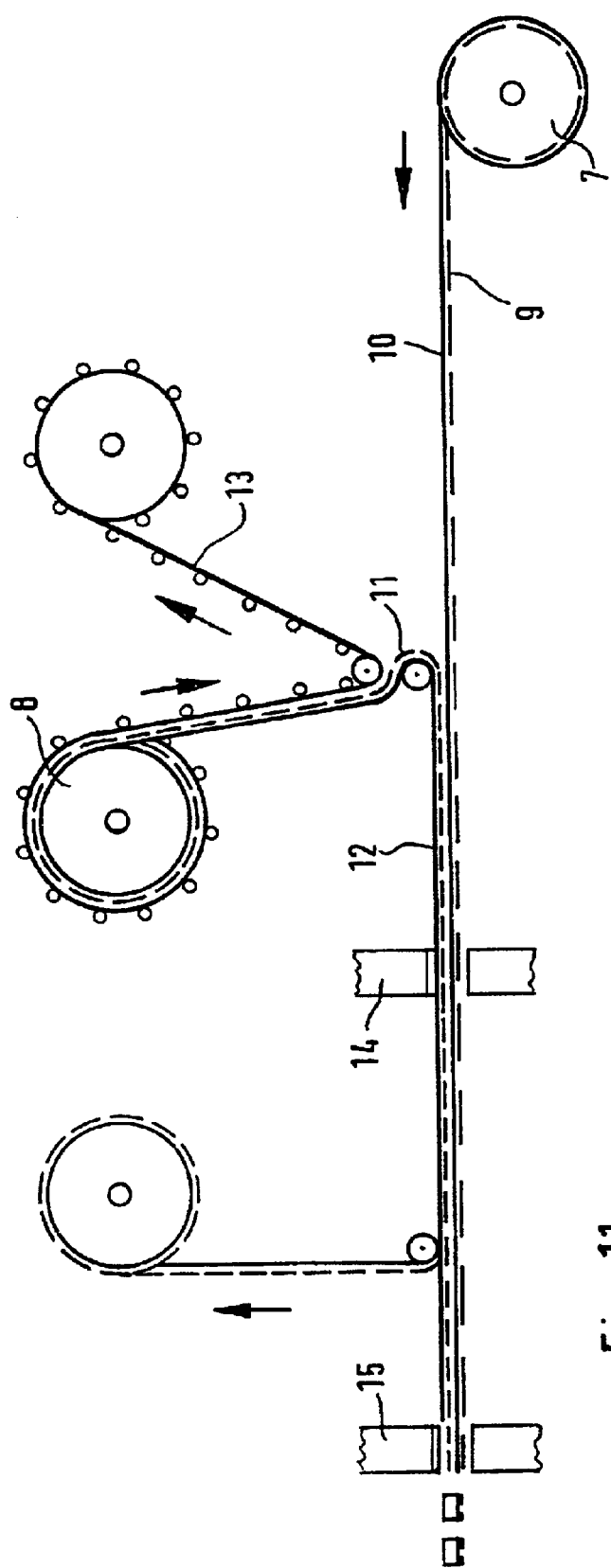

1

COMPOSITE LAMINATE AND METHOD FOR ITS PRODUCTION

This application is a 371 of PCT/EP00/04459 May 17, 2000.

BACKGROUND OF THE INVENTION

The invention relater to a composite laminate, in particular a transdermal therapeutic system (TTS), which comprises in at least one layer a moisture sensitive active substance and possesses a further layer, spatially separate from this active substance layer, which is capable of absorbing moisture, and to a process for producing such a composite laminate.

The transdermal administration of pharmaceutical active substances has been known from the time of the first commercial utilization of a scopolamine transdermal therapeutic system (Scopoderm TTS). Other active substances (nitroglycerine, estradiol, clonidine, isosorbide dinitrate, fentanyl, nicotine, norethisterone, etc.) have since been offered in the form of such a TTS. The layer-constructed active substance patches are adhered to the skin of a patient. The active substance can then be released from the TTS to the skin of the patient in a controlled manner.

Various types of such TTS have been described, for example, by Y. W. Chien in "Developmental Concepts and Practice in Transdermal Therapeutic Systems", in *Transdermal Controlled Systemic Medications*, ed. by Y. W. Chien, Marcel Dekker, Inc., New York (1982), Chapter 2, pp. 25–81. Accordingly, essential elements of a TTS are the active substance impermeable backing layer, an active substance reservoir or matrix layer, an optional semipermeable or microporous membrane to control the release of the active substance from the reservoir, an optional pressure sensitive adhesive layer, and an abhesive protective layer (release liner) which is removed from the pressure sensitive adhesive, skin contact side of the TTS before the TTS is used. In order to avoid repetition, the content of said chapter—especially the TTS types described therein—is hereby incorporated by reference as part of the disclosure of the present description. Owing to its layer construction, therefore, a TTS is a composite laminate, i.e., a device constructed of at least two layers.

One problem which may occur during the production and storage of TTS derives from the sensitivity of individual components, especially certain active substances, to moisture. This means that exposure even to small amounts of water may be accompanied by a physical and/or chemical transformation of the component and/or active substance, a consequence of which is that said component may lose its structural integrity or that the full activity of said active substance is no longer available for the pharmaceutical application.

Examples of substances, especially pharmaceutical active substances, which may suffer the abovementioned transformations on exposure to moisture are acetylsalicylic acid (ASA) and 17β-estradiol. In the case of acetylsalicylic acid there is a chemical reaction (hydrolysis), forming salicylic acid and acetic acid. In the case of 17β-estradiol there is a physical transformation (crystallization), forming hydrated crystals of poor solubility. As a consequence of these transformations, the pharmaceutical active substance is present dissolved in a reduced concentration in the various layers of the TTS, especially the matrix layer, the reservoir, and/or the pressure sensitive adhesive layer. In general, however, the desire is for a high concentration of dissolved active substance in the various layers of the TTS, especially the skin contact layer, in order to ensure a sufficiently large concentration difference between skin contact layer and the skin of the patient throughout the period of application of the TTS. It is this concentration difference, in fact, which is the driving force for the diffusion of the active substance into the skin and the blood circulation.

In order to prevent the problem of crystallization of the active substance owing to moisture exposure, various methods and means have been developed in order to reduce the culprit moisture content in the TTS-containing device—which in this case is the primary packaging, usually a sealed pouch.

Thus in DE 42 37 453 it has been proposed to produce and store the transdermal therapeutic systems comprising the moisture sensitive active substance 17β-estradiol under conditions of reduced atmospheric humidity. This was done by including a desiccant, in the form of several grains of blue gel, with the TTS in the sealed pouch.

DE 196 46 048 describes packaging for transdermal therapeutic systems which comprises an internally fixed drying device. The drying device is of flat construction and comprises a solid desiccant. Said drying devices are produced in a multistage process. In a first operation, the desiccant label must be produced by individualization from a desiccant laminate in web form; in a second operation it must be provided with an intermediate liner; and in a third operation, involving the removal of this abhesive intermediate liner, it must be positioned precisely on the web which produces the subsequent interior of the sealed pouch, and firmly and permanently bonded. In a further, separate operation, the TTS comprising the active substance in question must be produced. Finally, said TTS must be placed on the sealing pouch laminate web on which the individual desiccant labels have been bonded, and this web must be cut and sealed in such a way that the desiccant label does not lie on the resulting weld seams. The execution of these different operations and processes must be carried out in the absence of or with greatly reduced atmospheric humidity, which may additionally necessitate rapid working. Owing, however, to the required accuracy in the positioning of the desiccant label on the laminate, and in the positioning of the TTS on the laminate thus bonded, this is very technically demanding and/or very complex in terms of apparatus.

It is an object of the present invention to provide a device by means of which a composite laminate, especially a transdermal therapeutic system (TTS), which comprises in at least one layer a moisture-sensitive component, especially a moisture sensitive active substance, can be stored in a closed gas space under reduced atmospheric humidity, and a process for producing such a device. The intention is to provide devices with a simpler construction and processes which avoid the difficulties depicted in the production of the prior art devices.

BRIEF SUMMARY OF THE INVENTION

This object is achieved in accordance with the present invention by means of a composite laminate comprising at least two different layers. The composite laminate of the invention comprises at least one moisture sensitive layer (1) which comprises a moisture sensitive component. The composite laminate of the invention further comprises a moisture absorbing layer (2) which is free from active substance and is capable of absorbing moisture. The two separate layers can be adjacent and in direct contact with one another; preference is given, however, to embodiments in which these two layers are spatially separate from one another. Said composite laminate may preferably comprise a transdermal therapeutic system comprising at least one moisture-sensitive active substance.

BRIEF DESCRIPTION OF THE SEVERAL VIEWS OF THE DRAWING(S)

FIG. 11 is a schematic illustration of an advantageous process in accordance with the invention.

DETAILED DESCRIPTION OF THE INVENTION

Figure 1:
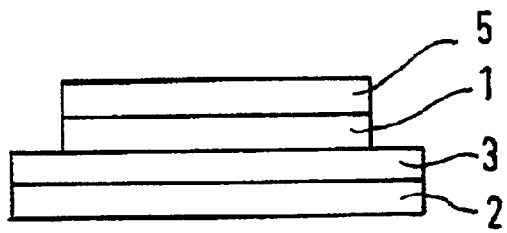
FIG. 1 is a schematic cross-sectional representation of one exemplary composite laminate in accordance with the invention.

The device of the invention comprises at least one moisture sensitive layer (1). The moisture sensitivity of this layer derives from the fact that it comprises a moisture sensitive component This includes a moisture sensitive material from which the layer is constructed and which therefore has essentially a carrier function. Such materials consist generally of one or more polymeric base materials. These are materials composed of molecules in which one or more types of atoms or atom groups are present in repeating series. Examples of moisture sensitive polymeric base materials may include polyvinyl acetate, polyvinyl alcohol, polyvinyl-pyrrolidone, polyanhydrides, biopolymers, cellulose, cellulose products, water-swellable polymers, and other macromolecular substances which dissolve, swell or undergo chemical transformation on exposure to moisture (essentially water).

In general, however, the component giving rise to the moisture sensitivity of this layer is a moisture sensitive substance present in said layer. This substance possesses no particular carrier function in the composite laminate of the invention, but instead constitutes the actual active principle to be carried. Such moisture sensitive substances may include pharmaceutical active substances, especially the active substances acetylsalicylic acid and 17β-estradiol, already mentioned, but also nicotine, morphine, diamorphine, lobeline, norethisterone acetate, fentanyl, lobeline, selegiline, testosterone and hydrolytically sensitive esters. The moisture sensitive substances may also, however, include substances having a relatively high molecular weight, such as, for example, insulin and other known proteins.

The device of the invention further comprises a moisture absorbing layer (2) which is free from active substance. A layer of this kind with moisture absorption capacity may consist, for example, of at least one polymeric material which is moisture absorbent or comprises a desiccant. The suitable polymeric materials include those which are permeable to moisture. Examples of moisture absorbing polymeric materials are polymers containing an N=C=N unit (the carbodiimide structural element).

Alternatively, polymeric materials can be used which have no moisture absorption capacity but serve merely as carrier material for the desiccant proper. Polymeric materials of this kind include polyethylene, polypropylene, polyacrylate, polyisobutene, polystyrene, polyvinyl chloride, polyvinylidene chloride, synthetic rubber, silicones, ethylene-vinyl acetate, and other elastomers and thermoplastics known to the skilled worker.

The suitable desiccants include, in particular, solids. Such solids include minerals such as silica gel, molecular sieve, calcium sulfate ($CaSO_4$, anhydrite), alumina $Al_2O_3$, calcium oxide CaO, potassium carbonate $K_2CO_3$, sodium carbonate $Na_2CO_3$, sodium sulfate $Na_2SO_4$, and other solids suitable as desiccants and known to the skilled worker, and mixtures thereof.

The moisture absorbing polymeric material or the desiccant is located in the moisture absorbing layer (2) in an active state in which the moisture absorbing polymeric material or the desiccant present in said layer is capable of absorbing moisture (water molecules). It may be necessary to convert said desiccant beforehand from an inactive state in which it is incapable of absorbing moisture into this active state. The moisture absorbing polymeric material and/or the desiccant itself is incapable or capable only to a very small extent of emerging (diffusing) from the moisture absorbing layer, i.e., it is practically immobilized in this layer.

In certain embodiments, the moisture absorbing layer (2) may judiciously be pressure sensitive adhesive, although in certain configurations it may also not be pressure sensitive adhesive or at least may be pressure sensitive adhesive on one side only. In order to make the moisture absorbing layer (2) pressure sensitive adhesive, it may be necessary to use pressure sensitive adhesive polymers as the polymeric material or to use polymers which are not pressure sensitive adhesive and to add tackifiers. Pressure sensitive polymers and/or polymers which are not pressure sensitive but with suitable tackifiers are known to the skilled worker. Pressure sensitive adhesive polymers include, for example, polyacrylates, polyisobutene, and silicones; examples of tackifiers are resins such as rosin.

In order to make the moisture absorbing layer (2) pressure sensitive adhesive on one side only, a nonadhesive layer must be laminated onto one side of the pressure sensitive adhesive, moisture absorbing layer.

The moisture content of the moisture sensitive layer (1) can be kept constant and/or below a certain desired limit by the simultaneous presence of the moisture absorbing layer (2) in the device. In one preferred embodiment the moisture content of the moisture sensitive layer (2) is below 0.5% by weight; in a particularly preferred embodiment the moisture content of the moisture sensitive layer (2) of the composite laminate is below 0.2% by weight.

The spatial separation of these two different layers (1) and (2) within the composite laminate is a further feature of said laminate in certain embodiments. Said spatial separation of the two different layers can be achieved in various ways. In one case there is a horizontal separating layer (3) between the two layers, in the other case a vertical separating layer (4).

This separating layer possesses the function of preventing the entry of desiccant into the moisture sensitive layer (1) and/or the entry of the moisture sensitive component into the moisture absorbing layer (2). Where, however, the entry of moisture absorbent polymeric material and/or of desiccant into the moisture sensitive layer (1) and/or the entry of the moisture sensitive component into the moisture absorbing layer (2) does not take place in practice and/or at least has no deleterious effects on the layer in question, the use of such an additional separating layer can be omitted. In an embodiment of this kind the moisture sensitive layer (1) and the moisture absorbing layer (2) can be present in two separate layers adjacent to one another, especially one atop the other, and can be in direct contact with one another.

A specific embodiment of a horizontal separating layer (3) is a protective layer disposed below the moisture sensitive layer (1) and above the moisture absorbing layer (2). This case constitutes a very simple and thus preferred embodiment. It is shown in FIG. 1. FIG. 1 shows a composite laminate with a horizontal separating layer (3), a single-sidedly pressure sensitive adhesive, moisture absorbing layer (2) and a laterally open moisture sensitive layer (1). The horizontal separating layer (3) serves simultaneously as joint carrier layer of moisture sensitive layer (1) and moisture absorbing layer (2) and as protective layer (release liner) for the moisture sensitive layer (1). It is therefore identical with the protective layer of a conventional TTS. At the top, the moisture sensitive layer (1) is covered by the backing layer (5), which can in turn be moisture permeable or moisture impermeable.

Figure 2:
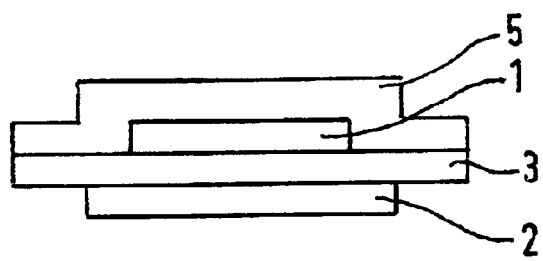
FIG. 2 is a schematic cross-sectional representation of a further exemplary composite laminate in accordance with the invention.

The moisture absorbing layer (2) is preferably congruent with the horizontal separating layer (3), but may also be smaller than the area of the horizontal separating layer (3). In this embodiment, the moisture absorbing layer (2) is single-sidedly pressure sensitive adhesive, so that it is firmly connected to the horizontal separating layer (3) and is removed together with this layer, which serves simultaneously as protective layer, not until immediately before the application of the remaining layers of the composite laminate (i.e., of the TTS that is actually to be applied). The horizontal separating layer (3) may be impermeable to moisture; preference is given, however, to an embodiment which is permeable to moisture but at the same time impermeable to the moisture sensitive component When a moisture impermeable horizontal separating layer (3) is used, it is preferred to use a moisture permeable backing layer (5).

Where the backing layer (5) is moisture impermeable and at the same time closes off the moisture sensitive layer (1) completely, i.e., including lateral closing off with respect to the environment, a moisture permeable horizontal separating layer (3) is used which simultaneously constitutes the protective layer (6). A composite laminate of this kind is depicted in FIG. 2.

In another embodiment, the horizontal separating layer (3) consists of an intermediate layer disposed above the moisture sensitive layer (1) and below the moisture absorbing layer (2). In contrast to the embodiments depicted in FIGS. 1 and 2, this embodiment need not necessarily involve the separation of the moisture absorbing layer (2) directly before the TTS is applied. This depends on the construction of the composite laminate.

Figure 3:
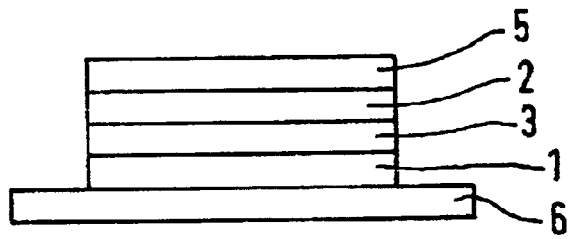
FIG. 3 is a schematic cross-sectional representation of a further exemplary composite laminate in accordance with the invention.

If the horizontal separating layer (3) is abhesive on the side facing the moisture absorbing layer (2) or if the side of the moisture absorbing layer (2) facing the horizontal separating layer (3) is abhesive, the moisture absorbing layer (2) including the backing layer (5) may be separated. This case is depicted diagrammatically in FIG. 3. In this case, the moisture absorbing layer (2) may, if desired, also be identical with the backing layer (5) of the composite laminate.

Figure 4:
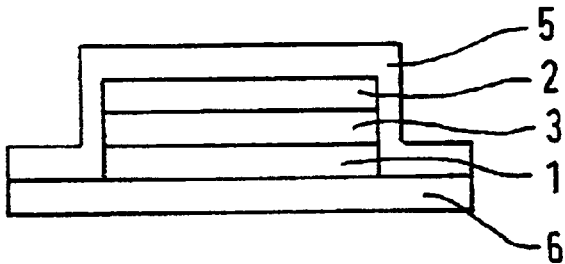
FIG. 4 is a schematic cross-sectional representation of a further exemplary composite laminate in accordance with the invention.

If, however, neither the horizontal separating layer (3) nor the moisture absorbing layer (2) is abhesive on at least one side, and/or if the assembly of these two layers is covered by a joint backing layer (5) which closes off completely the assembly of these layers with respect to the environment, separation of the moisture absorbing layer (2) is impossible. This case is shown in FIG. 4. The composite laminate depicted possesses a horizontal separating layer (3) which constitutes a moisture permeable intermediate layer within the device. Backing layer (5) and protective layer (6) dose off completely the assembly of moisture absorbing layer (2), horizontal separating layer (3) and moisture sensitive layer (1) with respect to the environment. In an embodiment of this kind, where the moisture absorbing layer (2) is applied together with the remaining layers of the device, it is possible for the desiccant present therein to be returned to the inactive state owing to water absorption during the period of use.

Figure 5:
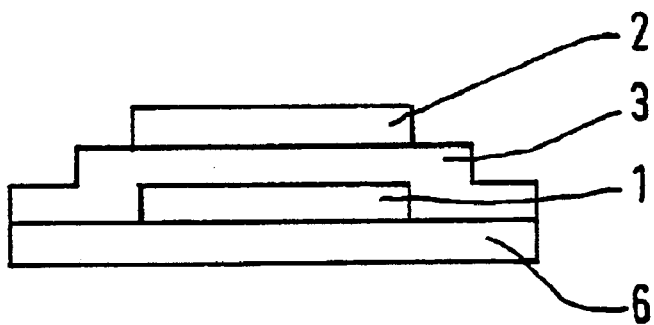
FIG. 5 is a schematic cross-sectional representation of a further exemplary composite laminate in accordance with the invention.

FIG. 5 shows how the moisture absorbing layer (2) can also be disposed above the conventional backing layer. In this case the horizontal separating layer (3) is identical with such a backing layer. Where the side of the horizontal separating layer (3) facing the moisture absorbing layer (2), or the side of the moisture absorbing layer (2) facing the horizontal separating layer (3), is abhesive, this layer (2) can be separated from the separating layer (3) before the TTS is applied.

The case of a vertical separating layer (4) is employed with preference when the intention is to produce a particularly flat device or when no suitable materials (e.g., a material which is moisture permeable but impermeable to the moisture sensitive components of the moisture sensitive layer) for a horizontal separating layer are available.

Figure 6:
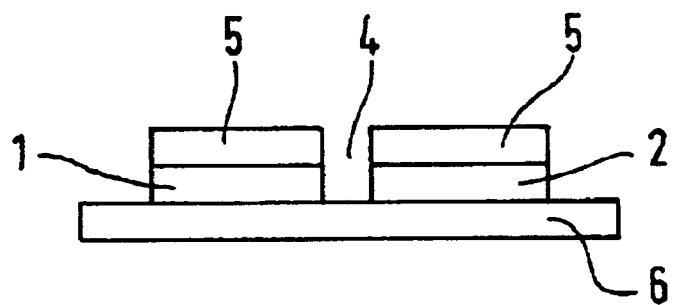
FIG. 6 is a schematic cross-sectional representation of a further exemplary composite laminate in accordance with the invention.

The simplest embodiment of the composite laminate of the invention comprising a vertical separating layer (4) is depicted in FIG. 6. In this embodiment, the vertical separating layer (4) consists of a material void (a gap; an air-filled, otherwise empty space) between the moisture sensitive layer (1) and the moisture absorbing layer (2). The backing layers (5) can be identical or different.

Figure 7:
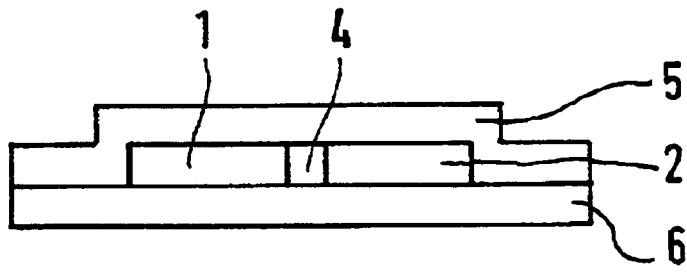
FIG. 7 is a schematic cross-sectional representation of a further exemplary composite laminate in accordance with the invention.

Alternatively, the vertical separating layer (4) can comprise a solid material which is permeable to moisture and at the same time essentially impermeable to the moisture sensitive components of the moisture sensitive layer (1). FIG. 7 shows a composite laminate of this kind with a vertical separating layer (4) comprising such a material. The backing layer (5) closes off the moisture sensitive layer (1) and the moisture absorbing layer (2) completely with respect to the environment.

In the embodiments with a vertical separating layer (4), moisture sensitive layer (1) and moisture absorbing layer (2) adhere to the same side of a single protective layer (6).

The moisture sensitive layer (1), the moisture absorbing layer (2) and the vertical separating layer (4) can possess different backing layers (5) or the same backing layer (5).

In the embodiments with a vertical separating layer (4), the geometric shape of moisture absorbing layer (2) and/or moisture sensitive layer (1) is in principle uncritical. A rectangular or square shape is preferred.

It is possible for the moisture absorbing layer (2) to be separated together with the protective layer (6) from the other layers of the composite laminate before the actual TTS is applied. This is possible, for example, in the embodiment of FIG. 6. If an embodiment as in FIG. 7 is used, this is not possible.

Figure 8:
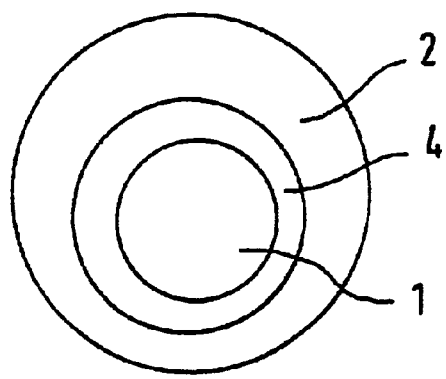
FIG. 8 is a schematic cross-sectional representation of a further exemplary composite laminate in accordance with the invention.

FIG. 8 shows a further composite laminate in which the moisture absorbing layer (2) is disposed annularly around a central circular moisture sensitive layer (1) separated by an annular vertical separating layer (4). It is clear that in such a manner it is also possible in principle for the moisture sensitive layer (1) to be disposed annularly around a circular moisture absorbing layer (2).

Figure 9:
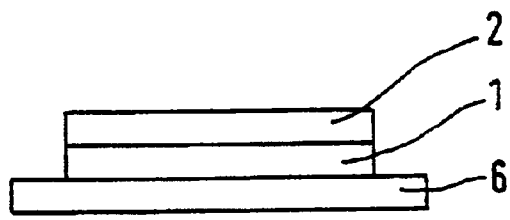
FIG. 9 is a schematic cross-sectional representation of a further exemplary composite laminate in accordance with the invention.

FIG. 9 shows a composite laminate in which the moisture sensitive layer (1) and the moisture absorbing layer (2) are present adjacent one another in two separate layers and are in direct contact with one another. An additional separating layer between them has been omitted owing to the absence of the above-described interactions, caused essentially by the diffusion of constituents of the one layer into the other layer.

Figure 10:
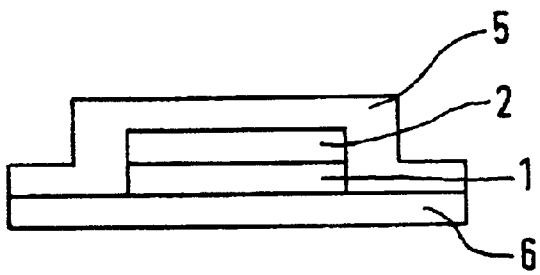
FIG. 10 is a schematic cross-sectional representation of a further exemplary composite laminate in accordance with the invention.

FIG. 10 shows an embodiment as in FIG. 9, except that the assembly comprising moisture sensitive layer (1) and moisture absorbing layer (2) is additionally covered by a backing layer (5). By this means, moisture sensitive layer (1) and moisture absorbing layer (2) are closed off completely with respect to the environment.

In all embodiments discussed and depicted, the other standard components of a TTS (backing layer, microporous and/or semipermeable membrane, additional pressure sensitive adhesive layer, nonwoven, etc.) can be disposed if desired around the moisture sensitive layer (1) or can be present in that layer itself.

The process of the invention comprises applying said at least one moisture sensitive layer (1) and said at least one moisture absorbing layer (2) to a carrier layer. The process comprises two or more steps, the two central steps of the process comprising the bringing together of the moisture sensitive layer (1) with a carrier layer and the bringing together of the moisture absorbing layer (2) with a carrier layer.

These two central steps of the process can, in accordance with the invention, take place in temporal and/or spatial succession. Alternatively, the two central steps of the process may take place simultaneously and/or in spatial vicinity. By spatial vicinity is meant that the two layers are placed directly alongside one another (i.e., at the distance of the vertical separating layer) on the same carrier layer. Spatial vicinity also means that the two layers are placed directly opposite on the top and bottom sides of the same carrier layer.

In the embodiments comprising a horizontal separating layer, the carrier layer can be the horizontal separating layer itself, and, in the embodiments comprising a vertical separating layer, the carrier layer can be a common carrier layer, e.g., a release liner serving as protective layer.

The production of the moisture sensitive layer (1) is known in principle to the skilled worker and can be carried out conventionally, e.g., by mixing the components such as polymeric material, active substance, and, if used, tackifier, plasticizer, solvent, crosslinker, etc., and applying the mixture as a coating and stripping off the solvent or extruding the mixture in the case of solvent free mixtures, etc. The components of said mixture also include, of course, the moisture sensitive component.

The production of a moisture absorbing layer (2) is also fundamentally known. It can be carried out in the same conventional ways as the production of the moisture sensitive layer (1). However, at least one moisture absorbing polymeric material and/or a desiccant are mixed with, if appropriate, at least one matrix material. In order to obtain a pressure sensitive adhesive, moisture absorbing layer, it may be necessary for the matrix material to be pressure sensitive adhesive or to add a tackifier to the mixture. This mixture is then coated onto an intermediate cover. In order, if desired, to make this pressure sensitive adhesive, moisture absorbing layer pressure sensitive adhesive on one side only, use is further made of a nonadhesive final cover.

One possible further step of the process is the activation of the moisture absorbing layer (2). By activation is meant the conversion of the desiccant present in said layer from an inactive state incapable of absorbing moisture into an active state capable of absorbing moisture. This can be done in various ways; for example, by heating at elevated temperatures and/or storage under extremely dry conditions and/or greatly reduced external pressure. Further methods and conditions for activating the desiccant are known to the skilled worker. The moisture absorbing layer (2) can be activated before the laminate comprising moisture absorbing layer (2), backing layer and moisture sensitive layer (1) has been produced. Alternatively, it can take place after this laminate has been produced, provided the conditions of activation do not exert any adverse effects on the moisture sensitive layer (1) or other components of this composite laminate. It is clear that, following the activation of the desiccant and/or when using a moisture absorbent polymeric material, the further subsequent steps of the process, or all steps of the process, should be carried out as far as possible with the exclusion of, and/or greatly reduced, atmospheric humidity and/or with particular rapidity. Further steps of the process when producing a composite laminate of the invention may be the following: laminative application of further components, such as a backing layer (5), an additional, nonwoven layer, a semipermeable or microporous membrane, an additional pressure sensitive adhesive layer, and further protective layers on the moisture sensitive layer (1) and/or the moisture absorbing layer (2).

With respect to the central steps of the process, the point in time at which these further steps of the process are performed depends on the structure which the composite laminate of the invention is ultimately intended to have. The skilled worker knows whether a corresponding step of the process is to be conducted before, simultaneously with or after the central working steps. Thus it may be advantageous, for example, to attach a joint additional backing layer (5) following production of the composite laminate comprising moisture sensitive layer (1) and moisture absorbing layer (2), whereas the attachment of a membrane to the moisture sensitive layer (1) before the composite comprising moisture sensitive layer (1) and moisture absorbing layer (2) is produced may be more judicious.

Concluding steps of the process are the individualization of the composite laminate by cutting or punching and the accommodation of the individualized products (punched products) of the composite laminate (especially individual TTS) into corresponding seal pouches or thermoformed blisters.

The problem on which it is based is solved by the present invention in a surprising and particularly simple manner. One advantage is that the moisture absorbing layer is now present directly in the device which also comprises the moisture sensitive layer. The embodiments depicted also largely avoid possible problems of incompatibility between the ingredients of the moisture sensitive layer and those of the moisture absorbing layer. The process of the invention is simplified by the omission of separate production procedures for the desiccant laminate and the active substance laminate.

The example which follows is intended to elucidate the production of a composite laminate.

EXAMPLE 1

A first stock roll (7) has on it a conventionally produced, single-sidedly pressure sensitive adhesive layer (9) which contains $CaSO_4$ and is covered with an abhesive protective film (10). A second stock roll (8) has on it a layer (11) comprising the active substance 17β-estradiol as moisture sensitive component. This moisture sensitive layer (11) is likewise pressure sensitive adhesive and is equipped with a backing layer (12) and with an abhesive intermediate cover (13).

The laminate on the first stock roll (7) is unrolled. The intermediate cover (13) is removed from the laminate on the second stock roll (8), and the pressure sensitive adhesive side of the moisture sensitive layer (11) is applied to the reverse of the protective film (10) of the laminate unrolled from the first stock roll (8).

On a downstream lift punch (14) the contours of the patch are stamped from the laminate comprising backing layer (12) and moisture sensitive layer (11). The projecting edge is removed by lattice stripping. On a further punch device, pimples and/or removal aids in the form of notches are punched into the protective film (10).

Finally, the protective film, together if appropriate with the desiccant layer, is separated on a further punch device (15), e.g., a lift punch. The composite laminates individualized by transverse cutting in this way are placed on a web of a sealable material and are sealed in conventional manner.

The procedure described in this example is shown diagrammatically in FIG. 11.

I claim:

1. A composite laminate comprising at least two different layers, wherein a first layer is a moisture sensitive layer (1) which comprises a moisture sensitive component selected from the group consisting of moisture sensitive polymeric materials and moisture sensitive pharmaceutical active substances, and a second layer is a moisture absorbing layer (2) which comprises a desiccant in an activated state, wherein a spatial separation of the two different layers prevents the entry of said desiccant into the moisture sensitive layer (1) and/or the entry of the moisture sensitive component into the moisture absorbing layer (2).

2. The laminate according to claim 1, wherein a horizontal separating layer (3) or a vertical separating layer (4) brings about spatial separation of the moisture sensitive layer (1) from the moisture absorbing layer (2).

3. The laminate according to claim 1, wherein the moisture sensitive polymeric material is at least one macromolecular substance which dissolves, swells or undergoes chemical transformation upon exposure to moisture and is selected from the group consisting of polyvinyl acetate, polyvinyl alcohol polyvinylpyrrolidone, polyanhydride, cellulose, cellulose products, biopolymers, water swellable polymers and proteins.

4. The laminate as claimed in claim 1, wherein the moisture sensitive pharmaceutical active substance is selected from the group consisting of acetylsalicylic acid, 17β-estradiol, nicotine, morphine, norethisterone acetate, fentanyl, lobeline, selegiline, testosterone, protein, and hydrolytically sensitive esters that are capable of losing their full activity upon exposure to moisture.

5. The laminate as claimed in claim 1, wherein the moisture absorbing layer (2) is pressure sensitive adhesive on at least one side.

6. The laminate as claimed in claim 1, wherein the desiccant is a single substance comprising at least one member selected from the group consisting of silica gel, molecular sieve, $Na_2SO_4$, $Na_2CO_3$, $CaSO_4$, $Al_2O_3$, CaO, $K_2CO_3$ and mixtures thereof.

7. The laminate as claimed in claim 1, which is a transdermal therapeutic system.

8. A process for producing a composite laminate comprising at least one moisture sensitive layer (1) which comprises a moisture sensitive polymeric material and/or a moisture sensitive pharmaceutical active substance, and at least one moisture absorbing layer (2) which comprises a desiccant in an activated state, said two layers being spatially separated from one another, which comprises applying a moisture absorbing layer (2) and a moisture sensitive layer (1) to a carrier layer in two component steps.

9. The process as claimed in claim 8, wherein the two component steps take place in temporal and/or spatial succession.

10. The process as claimed in claim 8, wherein the moisture absorbing layer (2) and the moisture sensitive layer (1) are applied to opposite sides or to the same side of the carrier layer.

11. The process as claimed in claim 8, wherein the moisture absorbing layer (2) is activated in a Her step before or after the production of the composite laminate comprising moisture absorbing layer (2), carrier layer and moisture sensitive layer (1).

12. The process as claimed in claim 8, wherein individual punched products are produced by punching or cutting in a further step following production of the composite laminate comprising moisture absorbing layer (2), carrier layer and moisture sensitive layer (1).

13. The process as claimed in claim 12, wherein the individual punched products are further transferred to a thermoformed blister or a sealable web and are covered with a scalable web, and sealed and cut.

14. A composite laminate according to claim 1, wherein the spatial separation is implemented by means of a horizontal separating layer (3).

15. A composite laminate according to claim 1, wherein the spatial separation is implemented by means of a vertical separating layer (4).

* * * * *